United States Patent
Boring

(10) Patent No.: US 9,937,309 B2
(45) Date of Patent: Apr. 10, 2018

(54) METHOD OF OPTIMIZING THERAPY PRESSURE IN A BREATHING THERAPY MACHINE HAVING AN AUTO-ADJUST FEATURE

(71) Applicant: DeVilbiss Healthcare LLC, Somerset, PA (US)

(72) Inventor: Joseph J. Boring, Davidsville, PA (US)

(73) Assignee: DEVILBISS HEALTHCARE LLC, Somerset, PA (US)

( * ) Notice: Subject to any disclaimer, the term of this patent is extended or adjusted under 35 U.S.C. 154(b) by 743 days.

(21) Appl. No.: 14/337,897

(22) Filed: Jul. 22, 2014

(65) Prior Publication Data

US 2016/0022937 A1 Jan. 28, 2016

(51) Int. Cl.
*A61M 16/00* (2006.01)

(52) U.S. Cl.
CPC .... *A61M 16/0069* (2014.02); *A61M 16/0003* (2014.02); *A61M 16/022* (2017.08); *A61M 16/024* (2017.08); *A61M 2016/003* (2013.01); *A61M 2016/0027* (2013.01); *A61M 2205/3334* (2013.01)

(58) Field of Classification Search
CPC .................................................. A61M 16/0069
See application file for complete search history.

(56) References Cited

U.S. PATENT DOCUMENTS

| | | | | |
|---|---|---|---|---|
| 5,537,997 A | * | 7/1996 | Mechlenburg | A61M 16/00 128/203.16 |
| 5,704,345 A | * | 1/1998 | Berthon-Jones | A61B 5/087 128/204.21 |
| 6,105,575 A | * | 8/2000 | Estes | A61M 16/00 128/204.21 |
| 6,467,477 B1 | * | 10/2002 | Frank | A61M 16/024 128/203.23 |
| 6,932,084 B2 | | 8/2005 | Estes et al. | |
| 8,316,847 B2 | | 11/2012 | Hallett | |
| 2003/0111079 A1 | * | 6/2003 | Matthews | A61M 16/0051 128/204.18 |
| 2003/0127097 A1 | * | 7/2003 | Yurko | A61M 16/00 128/204.23 |
| 2005/0005937 A1 | * | 1/2005 | Farrugia | A61B 5/08 128/204.18 |
| 2005/0081854 A1 | * | 4/2005 | Nadjafizadeh | A61M 16/00 128/204.23 |
| 2005/0211248 A1 | | 9/2005 | Lauk et al. | |
| 2006/0000475 A1 | * | 1/2006 | Matthews | A61M 16/0051 128/204.21 |

(Continued)

FOREIGN PATENT DOCUMENTS

| | | |
|---|---|---|
| EP | 0788805 A2 | 8/1997 |
| WO | 2009/026582 A1 | 2/2009 |

OTHER PUBLICATIONS

Chen, et al., Control System Design for a Continuous Positive Airway Pressure Ventilator, Biomed. Eng. Online, 2012, 11:5.

(Continued)

*Primary Examiner* — (Jackie) Tan-Uyen T Ho
*Assistant Examiner* — Joseph D Boecker
(74) *Attorney, Agent, or Firm* — Carter, DeLuca, Farrell & Schmidt, LLP

(57) ABSTRACT

An improvement for existing breathing therapy machines which seeks the optimum therapy pressure using an auto-adjust algorithm.

19 Claims, 4 Drawing Sheets

(56) References Cited

U.S. PATENT DOCUMENTS

| | | | |
|---|---|---|---|
| 2006/0249149 A1* | 11/2006 | Meier | A61B 5/087 |
| | | | 128/204.18 |
| 2009/0107498 A1 | 4/2009 | Plattner et al. | |
| 2009/0205662 A1* | 8/2009 | Kwok | A61M 16/0051 |
| | | | 128/204.23 |
| 2011/0232643 A1* | 9/2011 | Mechlenburg | A61B 5/085 |
| | | | 128/204.23 |
| 2011/0240025 A1* | 10/2011 | Mechlenburg | A61M 16/026 |
| | | | 128/204.21 |
| 2011/0297156 A1* | 12/2011 | Shelly | A61M 16/00 |
| | | | 128/204.23 |
| 2012/0024286 A1 | 2/2012 | Boring | |
| 2012/0291785 A1 | 11/2012 | Ramanan et al. | |
| 2015/0040903 A1* | 2/2015 | Matthews | A61M 16/0051 |
| | | | 128/204.22 |
| 2015/0250963 A1* | 9/2015 | Ramanan | A61M 16/0069 |
| | | | 128/204.23 |
| 2015/0265789 A1* | 9/2015 | Whiting | A61B 5/04 |
| | | | 128/204.23 |
| 2015/0374940 A1* | 12/2015 | Froehlich | A61B 5/087 |
| | | | 128/204.21 |
| 2016/0015917 A1* | 1/2016 | Knepper | A61M 16/0069 |
| | | | 128/204.23 |
| 2017/0014585 A1* | 1/2017 | Gerred | A61M 16/0051 |
| 2017/0014587 A1* | 1/2017 | Whiting | A61B 5/087 |

OTHER PUBLICATIONS

European Search Report dated Jan. 30, 2018, corresponding to European Application No. 15825128.0; 5 pages.

* cited by examiner

METHOD OF OPTIMIZING THERAPY PRESSURE IN A BREATHING THERAPY MACHINE HAVING AN AUTO-ADJUST FEATURE

FIELD OF THE INVENTION

This invention is related to the field of breathing therapy machines, such as continuous positive airway pressure (CPAP) machines, which deliver air at a constant therapy pressure, and bi-level positive airway pressure (Bi-PAP) machines, which deliver air at a therapy pressure for inhalation and at a reduced pressure for exhalation. Such machines are typically used to treat patients suffering from breathing disorders, such as hypopnea or apnea. Specifically, the invention is related to such machines having an auto-adjust feature for automatically adjusting the therapy pressure delivered by the machine based on patient response.

BACKGROUND OF THE INVENTION

Continuous Positive Airways Pressure (CPAP) machines are well known in the art for use in the treatment of a number of respiratory conditions, such as sleep apnea and hypopnea, by supplying a continuous positive pressure to a patient's airway while the patient sleeps. A typical CPAP apparatus is programmed with a therapy pressure, and is able to maintain the set pressure (measured either at the mask or at a base unit) during the inhalation and exhalation phases of the breathing cycle. The pressure setting is typically programmed via a control on the unit. Bi-PAP machines will typically vary the positive pressure delivered to the user during the inhalation and exhalation phases of the breathing cycle. Typically, Bi-PAP machines deliver a lower pressure during the exhalation phase of the breathing cycle, to make it easier or less uncomfortable for patients to exhale while using the machine. The Bi-PAP machine is typically programmed with a therapy pressure, which is used as the inhalation pressure, while the exhalation pressure is typically a standard difference from the inhalation pressure.

FIG. 1 shows a schematic view of a typical prior art CPAP/Bi-PAP machine 30. Positive pressure is maintained by regulated blower 40, under control of motor control circuitry 38. Blower 40 supplies a pressurized flow of air to a mask connected via the flexible tube (not shown) to blower 40. Regardless of whether the device is a CPAP machine or a Bi-PAP machine, microprocessor 34, in accordance with normal operating programming stored in memory 36 produces a motor control signal which is interpreted by motor control circuitry 38. Motor control circuitry 38 translates motor control signal 37 into electrical impulses that control the speed of blower 40 to produce the desired pressure through flow element 42 and ultimately to the user of the device. The machine may be equipped with various sensors, such as pressure sensor 44 and flow sensor 46 to aid in the detection of sleep events. Control and programming of the device is accomplished via user interface 32.

Prior art breathing therapy machines may also be equipped with an auto-adjust feature. The auto-adjust feature allows the breathing therapy machine to adjust the pressure automatically in response to the sensed condition of the patient, specifically, in response to sensed apneas, hypopneas or episodes of periodic breathing. In a typical prior art implementation of this feature, the therapy pressure is quickly raised in response to sensed events, and then lowered in a linear manner until further events occur, at which time the cycle repeats. The auto-adjust feature is provided to make use of the machine more comfortable for the user and to avoid providing a higher pressure than is necessary to prevent or reduce events.

FIG. 2 shows a pressure graph produced by a common implementation of the auto-adjust feature. When the device detects a certain density of events (i.e., a certain number of events over a pre-determined period of time), for example, as shown in FIG. 2 as reference number 200, the pressure is aggressively raised as shown by reference number 210, until the events are eliminated or until the density of events is reduced below an acceptable level. Thereafter, the pressure is reduced in constant intervals at a slower rate as shown by reference number 220.

There are two problems with the prior art auto-adjust algorithm. First, the aggressive raising of pressure 210 often causes the delivered therapy pressure to overshoot the pressure needed to reduce or eliminate the events, and the slow rate of lowering the pressure 220 causes the therapy pressure to remain at a this higher level longer than necessary. This tends to cause the patient discomfort and may cause arousals during sleep. Secondly, the lowering of the pressure at the constant rate eventually allows the events to start occurring at a density high enough to cause the aggressive raising of pressure 210 to recur and begin the cycle again. This cycling over the course of a sleep session causes disruption in the patient's sleep.

Therefore, it would be desirable to provide an improved auto-adjust algorithm that alleviates these deficiencies in the prior art devices.

SUMMARY OF THE INVENTION

The present invention is a breathing therapy device having an improved auto-adjust algorithm that addresses the identified deficiencies in the prior art devices. When a predetermined density of events is detected, the improved auto-adjust algorithm acts identically to the prior art algorithm in aggressively raising the pressure to eliminate or reduce the events below the density threshold. Thereafter, however, instead of lowering the pressure in constant intervals, the pressure is quickly lowered (i.e., reduced at greater intervals) until a "transition" pressure threshold is reached. This addresses the first deficiency of the prior art algorithms, that being having the pressure remain at a higher than required level for longer than necessary.

After reaching the transition pressure transition point, the pressure is thereafter reduced in much smaller intervals, which tends to reduce the average rate of pressure reduction and to elongate the cycle such that the therapy pressure takes a much longer time to reach a pressure at which events previously occurred at a density high enough to restart the cycle. This has the effect of causing the cycle to repeat much less frequently than with the prior art algorithm, thus providing the patient with a sleep session having fewer disruptions.

DETAILED DESCRIPTION OF THE INVENTION

The improved auto-adjust algorithm of the present invention can be implemented in a typical prior-art device as a software module stored in memory 36. In the preferred embodiment, the algorithm is essentially two algorithms working concurrently, one to determine if the pressure should be raised, and the other to determine if the pressure should be lowered. As one of skill in the art would realize, this is only one way of implementing the invention, and other implementations may be used without deviating from the spirit or scope of the invention. In the preferred embodiment, both the pressure increase algorithm and the pressure decrease algorithm evaluate whether the pressure should be changed by determining the event density. Both algorithms are evaluated once a minute and look at the most recent 1 minute and 6 minute windows, as will be described below, to determine the event density. Preferably, the algorithms will be staggered to run at 30 second intervals.

Figure 1:
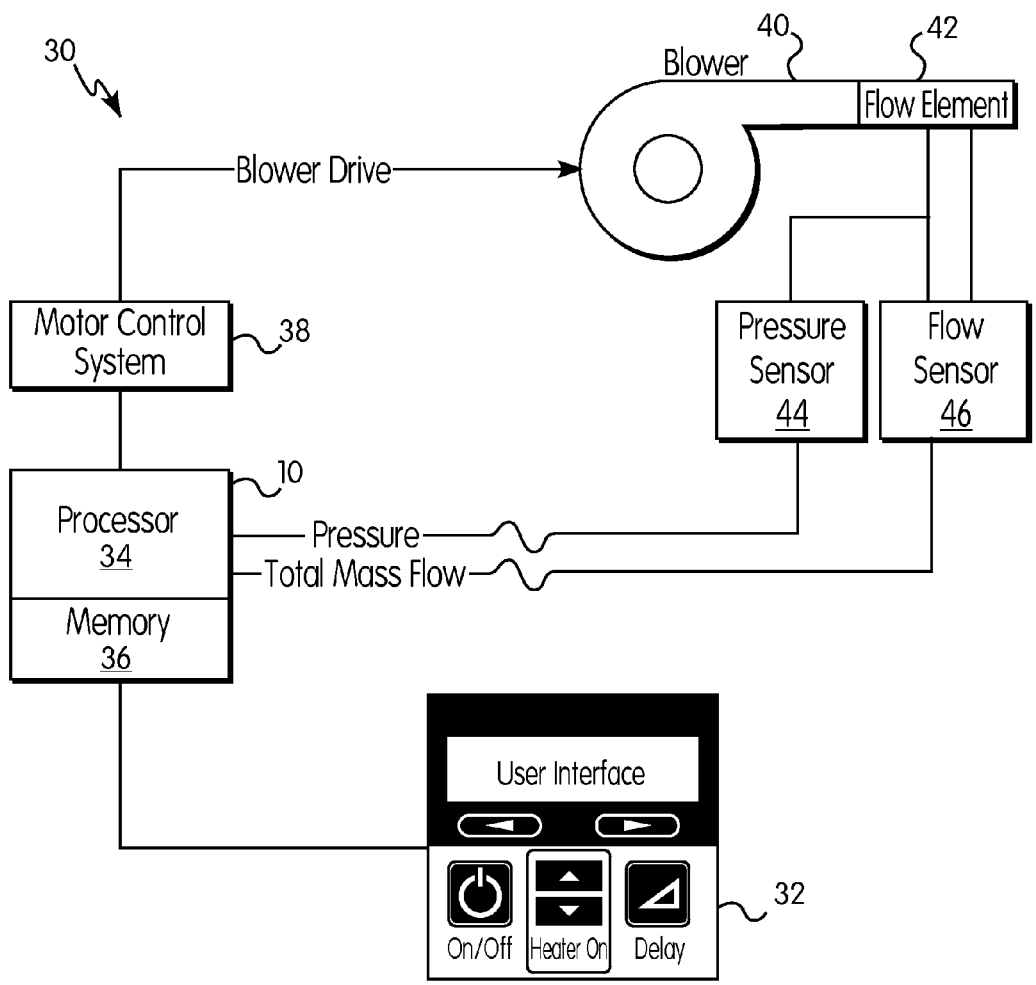
FIG. 1 is a schematic diagram of a prior art breathing therapy machine.
Figure 2:
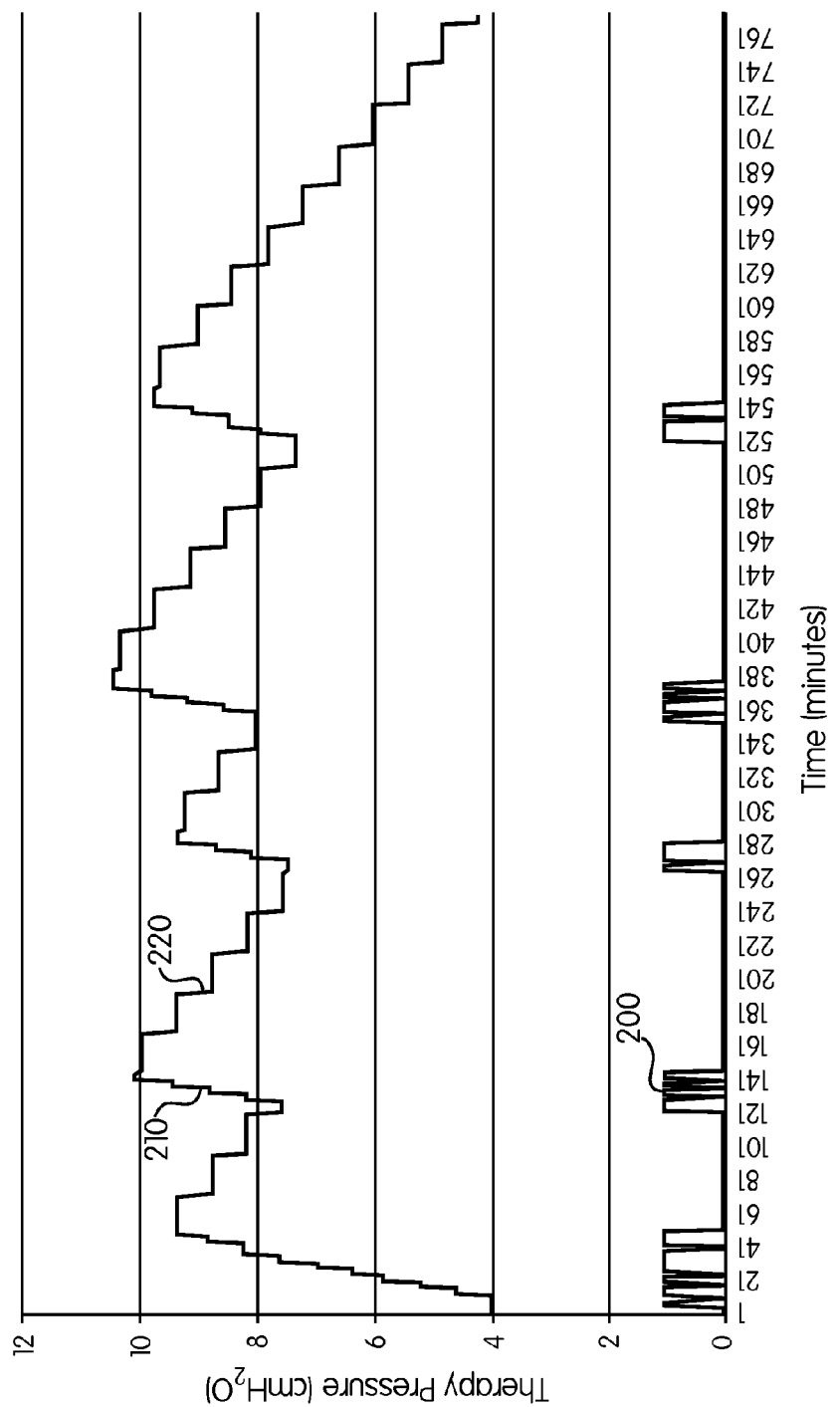
FIG. 2 is a graph showing pressure over time for a typical prior art implementation of an auto-adjust algorithm.
Figure 3:
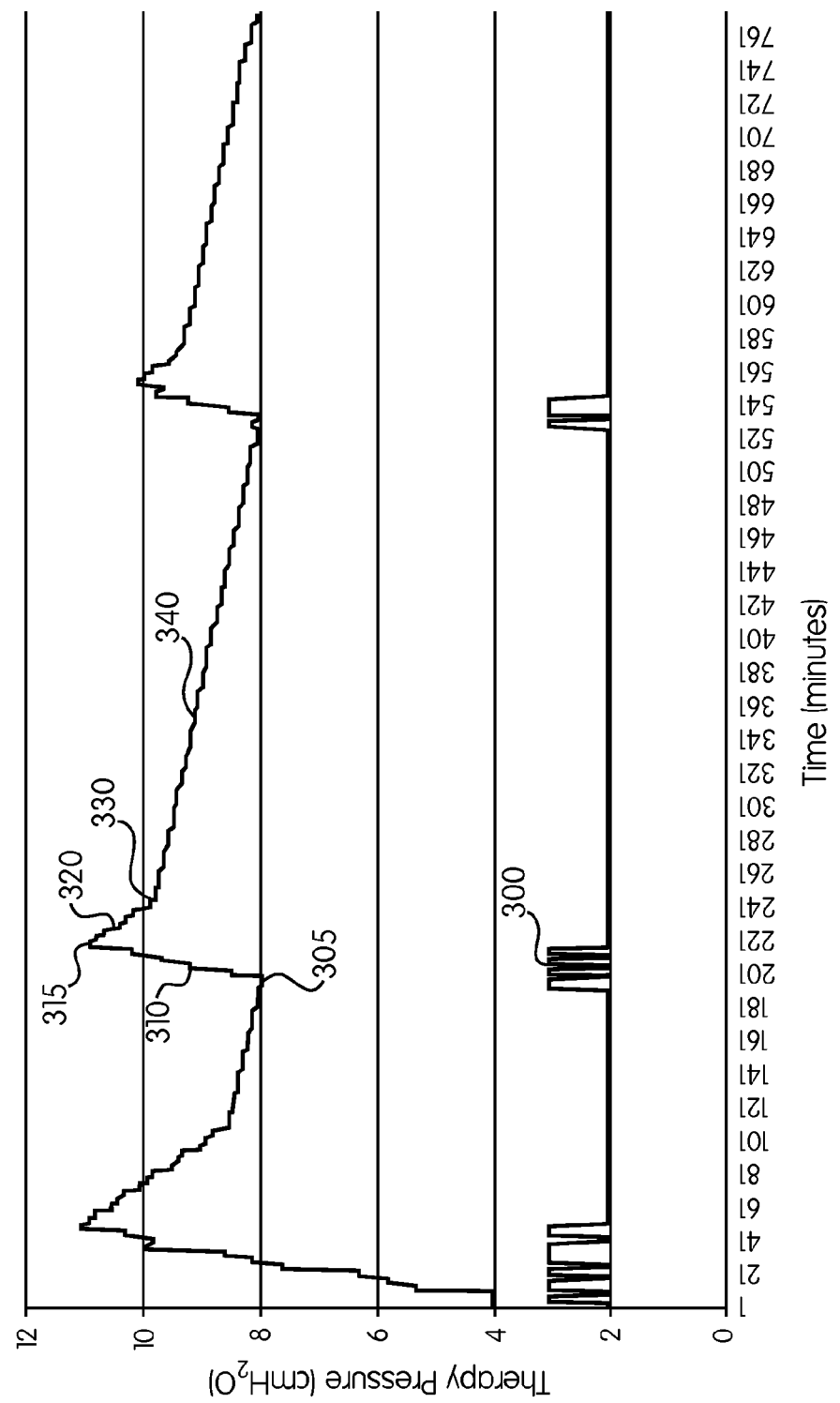
FIG. 3 is a graph showing pressure over time for the auto-adjust algorithm of the present invention.

A graph showing the results of the implementation of the algorithm of the present invention is shown in FIG. 3. The bottom plot shows events. Pressure increases are triggered when the event density exceeds a certain threshold, and the pressure continues to rise as long as at least one of the pressure increase algorithm triggering criteria are met. This phase of the cycle is shown by reference number 310 in FIG. 3. Because the pressure increases are aggressive and much higher than the pressure decreases generated by the pressure decrease algorithm, the increases in pressure during portion 310 of the cycle will overpower the much smaller decreases in pressure produced by the pressure decrease algorithm.

Although in the preferred embodiment, the criteria for determining the event density and resultant pressure increases is based on scientific observation of effective treatment regimens, many different criteria could be used to trigger increases in pressure. In the preferred embodiment, the following criteria are used by the pressure increase algorithm to determine if the pressure should be raised for any 1 minute evaluation cycle.

As previously stated, the event density is evaluated every minute, using the most recent 1 minute and 6 minute windows. Pressure increases will only occur if there have been no central events during the most recent 1 minute and 6 minute windows. The following criteria in the preferred embodiment will trigger a pressure increase:
- more than 2 obstructive events in the last 1 minute window (pressure rises by 1 cmH$_2$O);
- more than 1 obstructive event in the last 1 minute window and more than 2 obstructive events in the last 6 minute window (pressure rises by 1 cmH$_2$O); or
- 2 obstructive events in the last 1 minute window and 2 obstructive events in the last 6 minute window (pressure rises by of 0.5 cmH$_2$O).
- 1 or more RERA (Respiratory Effort Related Arousal) events in the last 1 minute window and 2 or more RERA events in the last 6 minute window (Pressure rises by 0.2 cmH$_2$O)

The event density will continue to be evaluated every minute and the rise in pressure will stop once none of the criteria are met, at a peak pressure point shown by reference number 315 in FIG. 3.

The pressure decrease algorithm is also evaluated every minute, although preferably staggered at 30 second intervals from the start of the pressure increase algorithm. During the initial phase of the pressure decrease portion of the cycle, as shown as reference number 320 in FIG. 3, the pressure decreases are relatively large, until the pressure transition point indicated by reference number 330 in FIG. 3 has been reached. The larger pressure decreases during portion 320 of the cycle helps in achieving the first goal of the invention, that being to decrease discomfort experienced by the patient and to reduce the likelihood of arousal during the sleep session.

After pressure transition point 330 has been reached, the pressure is decreased in much smaller increments, during the portion of the cycle indicated by reference number 340 in FIG. 3. The pressure transition point 330 is calculated in the preferred embodiment using the following equation:

$$\text{threshold} = \text{treatFloor} + 0.7 * (\text{maxTreatPressure} - \text{treatFloor}) \quad (1)$$

where treatFloor is the previous lowest pressure prior to the occurrence of an event and maxTreatPressure is the maximum system pressure used to treat the last event. FIG. 3 shows treatFloor as reference number 305, and maxTreatPressure as reference number 315. As one of skill in the art would recognize, the selection of 70% as the pressure transition point multiplier is arbitrary and could vary from that value, but should be most effective in the 60%-75% range.

The size of the pressure decreases in the initial rapid descent portion of the cycle 320, in the preferred embodiment, is given by the following criteria:
- more than 3 central events during the last 6 minute window (pressure decreases by 1.2 cmH$_2$O);
- at least 1 central event during the last 1 minute window (pressure decreases by 0.2 cmH$_2$O)
- 1 obstructive event and no central events in the last 1 minute window and less than 2 obstructive events and no central events in the last 6 minute window (pressure decrease by 0.1 cmH$_2$O)
- no obstructive or central events in the last 1 minute or 6 minute windows (pressure decreases by 0.1 cmH$_2$O)

Once pressure transition point 330 has been reached, the decreases in pressure are calculated using the same criteria as the pressure decreases prior to the pressure reaching pressure transition point 330, but are reduced by a percentage reduction to avoid having the event density rise sooner the necessary. In the preferred embodiment, if central events are present in the most recent 1 minute window, the rate of decrease after the pressure transition point 330 has been reached is reduced by 50% of the decrease calculated by the pressure reduction algorithm. If no central events are present in the most recent 1 minute window, the rate of reduction as calculated by the pressure reduction algorithm is reduced by 85%. The portion of the cycle having reduced reductions in pressure is shown by reference number 340 in FIG. 3. Note that, in the preferred embodiment of the invention, the percentages of reduction have been chosen arbitrarily and could be set to any value, as long as the average rate of reduction in the pressure in portion 340 of the cycle is less than the average rate of reduction in the pressure in portion 320 of the cycle, as shown in FIG. 3.

It should also be noted that, as the pressure is constantly decreasing, it is likely that the pressure will reach a point where the event density rises, as shown in FIG. 3 as reference 300, causing the pressure increase algorithm to generate pressure increases, as shown as reference number 310 in FIG. 3. However, in extending the time until the event density rises, the second goal of the invention has been met, that being that the cycle shown in FIG. 3 occurs less frequently during the course of the sleep session.

It should also be noted that current state-of-the-art machines can only make pressure changes in approximately 0.1 cmH$_2$O increments. Because many of the changes during portion 340 of the cycle are less than this amount, these pressure changes may be buffered until they accumulate to 0.1 cmH$_2$O or greater. This buffering of pressure changes does not change the overall average rate of reduction in the pressure.

Figure 4:
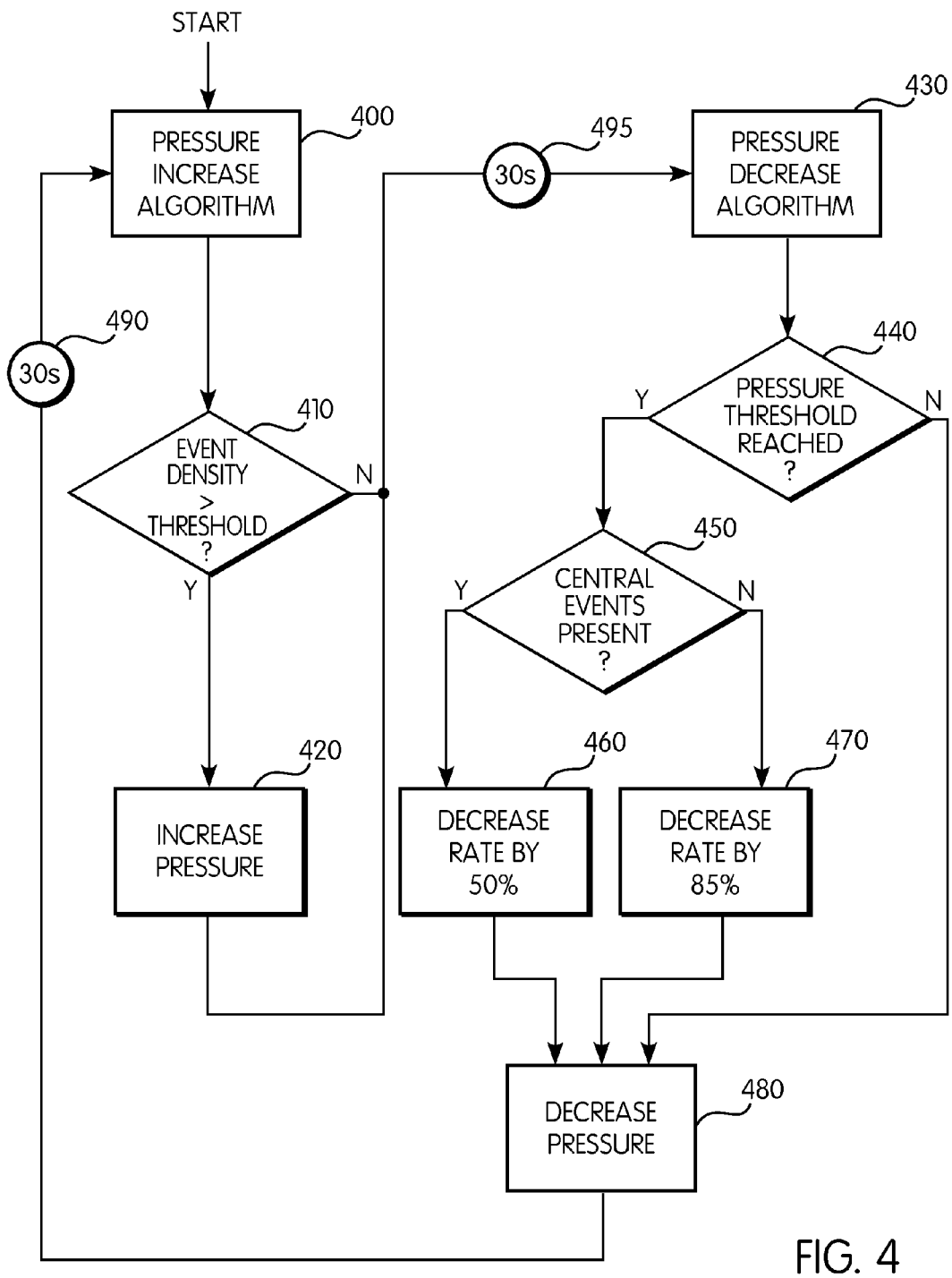
FIG. 4 is a flow chart showing the logic flow of the auto-adjust algorithm of the present invention.

FIG. 4 shows a flowchart of the auto adjust module of the present invention. As previously discussed, it consists of pressure increase algorithm 400 and pressure decrease algorithm 430. At the start, pressure increase algorithm 400 gathers data regarding events which have occurred during the most recent 1 minute and 6 minute windows. In box 410, a calculation is made to determine if the event density has exceeded the threshold for any of the criteria mentioned above. If the event density has exceeded the threshold this indicates that cycle is in portion 310 as shown in FIG. 3. Control then passes to box 420, where the increase in pressure is implemented and thereafter to a 30 second delay at 495, after which the pressure decrease algorithm 430 will be executed. If, in box 410, it is determined that the event density has not exceed the threshold specified by any of the criteria, then control proceeds directly to the 30 second delay 495.

In box 430 the pressure decrease algorithm determines the pressure decrease based upon the criteria mentioned above. In box 440, it is determined if the pressure transition point 330 has been reached. If not, control proceeds to box 480, where the calculated decrease in pressure is implemented. It should be noted that, if the "No" branch of box 440 is taken, this indicates that the cycle is either in portion 310 or 320 as shown in FIG. 3. If pressure transition point 330 has been reached (i.e., the pressure has previously been lowered to a level at or below pressure transition point 330), control proceeds to box 450, where it is determined if central events are present. If central events have been detected, control proceeds to box 460, where the rate of decrease in pressure is reduced by 50%. If, in box 450, no central events have been detected, then control proceeds to box 470, where the rate of decrease in pressure is reduced by 85%. In either case, control, from box 460 or 470, passes to box 480, where the decrease in pressure is implemented. Thereafter, control proceeds to 30 second delay 490 after which the pressure increase algorithm 400 is again executed.

With the 30 second delay 490, 495 between the execution of pressure increase algorithm 400 and pressure decrease algorithm 430, each algorithm is executed approximately once per minute, but at staggered intervals. This allows any previous changes in air pressure to become settled before another change in pressure is undertaken.

The invention has been explained in terms of a specific implementation utilizing specific numbers as criteria for pressure changes. As one of skill in the art will recognize that these specific values are merely exemplars and may be varied without deviating from the scope of the invention. In addition, FIG. 4 shows an implementation wherein the pressure decrease algorithm is executed even during portion 310 of the cycle. Many implementations are possible in which a more linear execution of the pressure increase algorithm and pressure decrease algorithm are utilized. Such implementations also fall within the scope of the invention. The invention is claimed in terms of net changes in pressure, regardless of whether, for example, a net increase in pressure consists of large increases and small decreases implemented concurrently.

I claim:

1. A breathing therapy machine having an auto-adjust capability comprising:
 a. a blower, for delivering air to a user of said device at a pressure;
 b. a processor, for controlling said blower;
 c. non-volatile memory, accessible by said processor, said non-volatile memory including operational programming; and
 d. an auto-adjust module, stored in said non-volatile memory as part of said operational programming, said auto-adjust module controlling said pressure of said air, wherein:
 said auto-adjust module applying a pressure cycle including a pressure increase portion, a first pressure decrease portion and a second pressure decrease portion, wherein each of said portions spans a plurality of inhalation and exhalation cycles;
 said auto-adjust module raises said pressure during said pressure increase portion in response to sensed events until said pressure has reached a peak pressure;
 said auto-adjust module lowers said pressure during said first pressure decrease portion from said peak pressure at a first averaged rate of decrease until said pressure reaches a pressure transition point that is calculated by the auto-adjust module based on the peak pressure and a lowest pressure applied before detection of the sensed events; and
 said auto-adjust module thereafter lowers said pressure during said second pressure decrease portion at a second averaged rate of decrease, said second averaged rate of decrease being lower than said first averaged rate of decrease.

2. The breathing therapy machine of claim 1 wherein said auto-adjust module raises said pressure in response to an event density that reaches or exceeds a predetermined pressure increase threshold.

3. The breathing therapy machine of claim 2 wherein said event density reaches or exceeds said pressure increase threshold when one or more criteria in a set of pressure increase criteria is met.

4. The breathing therapy machine of claim 3 wherein said pressure increase criteria are evaluated every minute over the most recent 1 minute and 6 minute windows of time.

5. The breathing therapy machine of claim 3 wherein said peak pressure is reached when said event density falls below said pressure increase threshold.

6. The breathing therapy machine of claim 5 wherein said auto-adjust module lowers said pressure in accordance with a set of pressure decrease criteria.

7. The breathing therapy machine of claim 6 wherein said pressure decrease criteria are evaluated every minute over the most recent 1 minute and 6 minute windows of time.

8. The breathing therapy machine of claim 7 wherein said pressure decrease criteria and said pressure increase criteria are evaluated at intervals which are staggered from each other.

9. The breathing therapy machine of claim 8 wherein said pressure decrease criteria and said pressure increase criteria are evaluated at intervals which are staggered 30 seconds from each other.

10. The breathing therapy machine of claim 6 wherein said pressure transition point is calculated as a percentage of the difference between said peak pressure and a lowest pressure reached before said peak pressure was reached at which said event density had reached or exceeded said predetermined pressure increase threshold.

11. The breathing therapy machine of claim 10 wherein the range of said percentage is 60%-75%.

12. The breathing therapy machine of claim 10 wherein said pressure decreases are calculated based upon periodic re-evaluation of said pressure decrease criteria.

13. The breathing therapy machine of claim 12 wherein pressure decreases after said pressure has reached said pressure transition point are determined by said periodic evaluation of said pressure decrease criteria and a percentage reduction rate is applied to a current calculated pressure decrease.

14. The breathing therapy machine of claim 13 wherein said pressure decreases before said pressure has reached said pressure transition point are averaged to obtain said first averaged rate of decrease and further wherein said pressure decreases after said pressure has reached said pressure transition point are averaged to obtain said second averaged rate of decrease.

15. The breathing therapy machine of claim 13 wherein said percentage reduction rate is a function of the type of events sensed as said pressure is decreased.

16. The breathing therapy machine of claim 15 wherein:
said percentage reduction rate is 50% if central type events have been detected during a most recent window of time; and
said percentage reduction rate is 85% if no central type events have been detected during said most recent window of time.

17. The breathing therapy machine of claim 16 wherein said most recent window of time is of a pre-determined length.

18. The breathing therapy machine of claim 1 further comprising:
one or more sensors capable of sensing events, said events including hypopneas and apneas and further wherein said events may be of the obstructive or central type.

19. A breathing therapy machine comprising:
a blower for delivering air at a pressure;
a processor configured to control the blower;
non-volatile memory which is accessible by the processor and which includes operational programming; and
an auto-adjust module, stored in the non-volatile memory as part of the operational programming, which is configured to control the pressure of the air by:
applying a pressure cycle which spans a plurality of inhalation and exhalation cycles and which includes a pressure increase portion, a first pressure decrease portion and a second pressure decrease portion;
raising the pressure during the pressure increase portion in response to sensed events until the pressure has reached a peak pressure;
lowering the pressure during the first pressure decrease portion from the peak pressure at a first averaged rate of decrease until the pressure reaches a pressure transition point that is calculated as a percentage of the difference between the peak pressure and a lowest pressure reached before the pressure was raised in response to the sensed events; and
lowering the pressure during the second pressure decrease portion at a second averaged rate of decrease, the second averaged rate of decrease being lower than the first averaged rate of decrease.

* * * * *